United States Patent [19]

Kaneko et al.

[11] 3,993,593

[45] Nov. 23, 1976

[54] CATALYSTS FOR THE PRODUCTION OF CARBONYL COMPOUNDS

[75] Inventors: Katsumi Kaneko; Toshio Hoshino, both of Saitama

[73] Assignee: Toa Nenryo Kogyo Kabushiki Kaisha, Tokyo, Japan

[22] Filed: Nov. 12, 1973

[21] Appl. No.: 414,777

[30] Foreign Application Priority Data

Nov. 22, 1972  Japan............................. 47-116566

[52] U.S. Cl................................ 252/441; 252/454; 252/460; 252/463; 252/474; 260/597 B
[51] Int. Cl.²...................... B01J 27/06; B01J 29/00; B01J 23/08
[58] Field of Search .......... 252/454, 456, 460, 463, 252/464, 441; 260/597 B

[56] References Cited
UNITED STATES PATENTS

| | | |
|---|---|---|
| 2,802,889 | 8/1957 | Frevel et al..................... 252/460 X |
| 3,228,991 | 1/1966 | Dulaney et al.................. 252/454 X |
| 3,239,448 | 3/1966 | Wilson............................ 252/454 X |
| 3,461,157 | 8/1969 | Olivier et al..................... 260/597 R |
| 3,701,810 | 10/1972 | Hasegawa et al. ............. 260/597 B |
| 3,787,514 | 1/1974 | Bernusset......................... 252/464 X |

*Primary Examiner*—Carl F. Dees
*Attorney, Agent, or Firm*—R. Yablonsky

[57] ABSTRACT

A one-step process is described for preparing carbonyl compounds by the oxidation of an olefin with oxygen in the presence of steam. A novel catalyst is used which is prepared by incorporating palladium and/or a palladium compound and copper chloride in a carrier comprising silica, alumina, or a mixture or complex oxide thereof, and calcining at a temperature in the range of 200°–400° C. One or more compounds of the group of silver, cerium and vanadium may optionally be included in the catalyst composition. Exemplary of the application of the method is the gas phase oxidation of butene to methyl ethyl ketone whereby high selectivity to desired product is obtained.

7 Claims, No Drawings

CATALYSTS FOR THE PRODUCTION OF CARBONYL COMPOUNDS

FIELD OF THE INVENTION

This invention relates to a process for producing carbonyl compounds from olefins and more particularly, it is concerned with a process for the production of carbonyl compounds by oxidizing olefins in one step in the presence of a novel catalyst.

DESCRIPTION OF THE PRIOR ART

As a method of producing carbonyl compounds from olefins, there has hitherto been proposed the Hoechst-Wacker process wherein acetaldehyde and acetone are produced from ethylene and propylene on a commercial scale. However, the production of methyl ethyl ketone (hereinafter referred to briefly as "MEK") from butene encounters more drawbacks, as compared with the production of ketones from ethylene or propylene, in that the reaction speed is low; n-butyl aldehyde, chlorobutanone and chlorinated butenes are formed as byproducts which necessitate complicated purification procedures; and marked corrosion occurs which is characteristic of the Wacker process.

In order to overcome these disadvantages, various methods of producing MEK by the gaseous phase oxidation of butene have been proposed such as by (1) using a catalyst prepared by the natural adsorption of palladium chloride on activated carbon (Japanese Patent Publication 5765/1970), (2) using a catalyst prepared by impregnating activated carbon with palladium chloride alone or together with a reoxidizer such as cupric chloride (U.S. Pat. No. 3,131,223; Japanese Patent Publication 7869/1961), (3) using a Pd-V compound as a catalyst (Japanese Patent Publication 1925/1972) and using a catalyst consisting mainly of Mo-Sn oxide (Japanese Patent Publications 8046/1972 and 11734/1972). However, these processes have not been satisfactory.

A novel catalyst system has now been found capable of forming carbonyl compounds, in particular MEK by the gaseous phase oxidation of butene, in high selectivity and without forming chlorobutanone and chlorinated products, and which shows higher activity than the catalyst systems (1) to (3) mentioned above.

SUMMARY OF THE INVENTION

According to the present invention, a process for the production of carbonyl compounds is provided which comprises reacting an olefin with oxygen in the presence of steam and a catalyst prepared by calcining at a temperature of 200°–400° C. a mixture of palladium and/or a palladium compound and copper chloride, supported by or formed with silica, alumina or a mixture or complex oxide containing silica and alumina; said mixture may optionally include one or more of silver, cerium and vanadium compounds.

As carrier, an acidic substance is used such as silica, alumina or a mixture or complex oxide containing silica and alumina; and calcining is essential. For example, natural or synthetic silica, alumina or zeolite, preferably colloidal alumina or colloidal silica, may be used. Incorporation of the catalytic components, i.e., palladium or its compounds and copper chloride is ordinarily accomplished by impregnation of, or mixing with said carrier. The catalyst of this invention may be prepared for example by adding an aqueous solution of the catalytic components to colloidal silica or alumina, concentrating, solidifying and shaping; or by adding the catalytic components to powdered silica or alumina and then forming the mixture.

As a palladium source of the catalytic compounds, metallic palladium or a palladium compound, for example, $PdCl_2$, $PdSO_4$, $Pd(NO_3)_2$, or $PdBr_2$ may be used; metallic palladium and $PdCl_2$ are preferred. As the copper chloride, cuprous chloride, cupric chloride and their mixture are suitable. Compounds of silver, cerium and vanadium, as the third component of this catalyst, are preferably $AgCl$, $CeCl_3$, $VOCl_2$, $VCl_3$ and $NH_4VO_3$. These third components are considered to have the effects of promoting the reoxidation of the Pd-copper chloride system as well as preventing the release of chloride ion from the catalyst system.

The ratios of the components are adjusted so that palladium is present in an amount of 0.1–10% by weight, preferably 0.5–5.0% by weight, as metal based on the carrier; copper chloride is present in a Cu/Pd atomic ratio of 0.5–50, preferably 1.0–30 and the third component is present suitably in a third component/Pd atomic ratio of 0.1–5.0.

After impregnation or mixing, the carrier supporting the catalytic components is dried, formed, and then calcined at a temperature of 200°–400° C., preferably 250°–350° C. for 5–10 hours in a gas such as air, nitrogen or argon or in gaseous hydrogen chloride, whereby a stable catalyst of high activity is obtained.

By calcining the carrier carrying the catalytic components within the above mentioned temperature range, the surface area of the catalyst is increased. The surface area and catalytic activity are found to be correlated in such a manner that the surface area reaches a maximum value within the optimum temperature range of 250°–350° C., whilst the surface area decreases at a temperature of less than 200° C. or more than 400° C. In particular, at above 400° C., the catalytic activity diminishes more markedly than the surface area. This is possibly due to other factors besides surface area.

The effects of the third component in the invention consist in increasing further the activity of the Pd-copper chloride catalyst system as well as preventing deterioration over a period of use.

By means of the catalyst prepared by the described method, MEK can be synthesized in high yield from n-butene and other carbonyl compounds can of course be produced effectively from the corresponding olefins such as ethylene, propylene and $C_5$- or higher olefins. When an olefin is, in particular, n-butene, butene-1, butene-2 (trans and cis) and their mixtures are useful as a starting material, but saturated hydrocarbons such as n-butane and isobutane may be included in the feed.

According to the process of the invention, production of a carbonyl compound from an olefin as raw material is carried out by contacting the olefin with oxygen or an oxygen-containing gas at 90°–200° C., preferably 110°–150° C. in the presence of steam. The method of contacting with the catalyst is either of the fixed bed or fluidized bed type. As the oxygen-containing gas, air or a mixture of oxygen with an inert gas such as nitrogen is suitably used. Steam may be supplied by supplying water to a preheating bed followed by evaporation. The mixing ratio of olefin, oxygen or an oxygen-containing gas and steam is, in the case of using n-butene and air, 1 (butene) : 1–20 (air) : 1–20 (steam) by volume and the space velocity of the mixed gas over a catalyst bed is preferably 200–2000 1/1-catalyst-hr. (N.T,P.).

A desired carbonyl compound can be obtained in high selectivity by means of the described method. When MEK is produced from n-butene, for example, the selectivity to MEK reaches 85–95%. Small amounts of n-butyl aldehyde, propionaldehyde, acetaldehyde, acetic acid and carbon dioxide are formed as by-products by advantageously chlorobutanone and chlorinated products of butene are not formed, which cause a problem in the previously mentioned liquid phase Wacker process.

PREFERRED EMBODIMENTS

The invention will now be illustrated in detail by the following examples, in which the yield of Product A, conversion ratio of butene and selectivity to Product A are calculated by the following equations:

$$\text{Yield of Product A (mol \%)} = \frac{\text{Moles of Product A}}{\text{Moles of n-butene supplied}} \times 100$$

$$\text{Conversion ratio (mol \%)} = \frac{\text{Moles of n-butene reacted}}{\text{Moles of n-butene supplied}} \times 100$$

$$\text{Selectivity to Product A (mol \%)} = \frac{(\text{Moles of Product A}) \times (\text{Carbon atoms of Product A})}{(\text{Moles of n-butene reacted}) \times 4} \times 100$$

EXAMPLE 1

1.6 g of palladium chloride dihydrate and 6.4 g of cupric chloride dihydrate were added to 200 ml of water and dissolved with heating at 60° C., to which 133 g of an aqueous 30% colloidal silica was added with adequate agitation. The resultant mixture was dried at 80° C. under reduced pressure, formed into pellets of 3 mm diameter and then calcined at various temperatures for 6 hours in air to prepare the catalysts. The content of palladium (metal weight %) in the catalyst was 2.0% based on the carrier of silica and the Cu/Pd atomic ratio was 5.0.

The oxidation reaction was continuously carried out at 125° C. by feeding a mixed gas of 1-butene, air and steam in a proportion by volume of 1 : 5 : 10 at various space velocities into a Pyrex glass reaction tube having an inner diameter of 15 mm, which was filled with 20 g of the so obtained catalyst and heated in an oil bath, whereby the results shown in Table I were obtained.

The composition of the reaction product after a running time of 4 hours in Run No. 4, for example, is shown below and scarcely any changes are found therein with the running time.

Conversion ratio of butene: 47.8%
Selectivities to reaction products:
  MEK 91.5%, n-butyl aldehyde 1.8%, acetaldehyde 0.4%, acetic acid 0.6%, carbon dioxide 1.3%, propionaldehyde trace The analysis by gas chromatography showed no formation of chlorobutanone and chlorinated products of butene.

For comparison, 1-butene was oxidized by the same method and procedure as described above except that a catalyst was used prepared by incorporating palladium chloride and cupric chloride in the support, drying and then forming similarly but not calcining (Run No. 8). As shown in Table I, the deterioration of this catalyst after use for a long time was greater as compared with the calcined catalyst.

For comparison, another catalyst was prepared according to the above mentioned Japanese Patent Publication 5765/1970. 0.8 g of palladium chloride was added to 200 ml of 0.5 N hydrochloric acid, heated at 60° C. to dissolve, and then 40 g of activated carbon (Trade Mark: Tsurumi Coal GW-30) was added thereto, followed by allowing to stand at room temperature for one day and night. The solution changed from brown to transparent and the palladium chloride was substantially absorbed on the activated carbon. The activated carbon was separated by filtration, washed with water treated with an ion exchange resin and dried at 150° C. for 3 hours under reduced pressure to prepare the catalyst. Oxidation of 1-butene was carried out with 20 g. of this catalyst by the same method and procedure as mentioned above (Run No. 9), but the yield of MEK was lower as compared with the catalyst of the invention as is evident from Table I.

Furthermore, oxidation of 1-butene was carried out with a catalyst prepared by the use of titanium oxide and magnesium oxide in place of the silica of this example (Run Nos. 10 and 11), but only lower activity was obtained as compared with using silica as a carrier, as shown in Table I.

TABLE I

| Run No. | Catalyst | Calcining temp. (° C) | Reaction temp. (° C) | Space velocity (hr⁻¹) | Yield of MEK (%) Running time (hrs.) | | | | | |
|---|---|---|---|---|---|---|---|---|---|---|
| | | | | | 2 | 4 | 6 | 8 | 24 | 48 |
| 1 | PdCl₂—CuCl₂/silica | 300 | 125 | 390 | 70.7 | 68.3 | 67.0 | 65.2 | 62.1 | 60.1 |
| 2* | " | 120 | " | 640 | 42.8 | 38.1 | 33.0 | 26.8 | 22.1 | 19.2 |
| 3 | " | 200 | " | " | 44.3 | 41.6 | 41.9 | 38.4 | 37.2 | 34.6 |
| 4 | " | 300 | " | " | 46.5 | 43.7 | 42.2 | 40.7 | 38.0 | 35.0 |
| 5 | " | 400 | " | " | 42.5 | 42.1 | 38.2 | 33.7 | 34.0 | 32.0 |
| 6* | " | 450 | " | " | 18.8 | 21.7 | 21.8 | 19.0 | 18.0 | 17.3 |
| 7 | " | 300 | " | 1100 | 39.7 | 36.0 | 32.7 | 30.0 | 28.1 | 26.5 |
| 8* | " | None | " | 640 | 42.2 | 40.0 | 38.8 | 37.4 | 25.3 | 15.5 |
| 9* | PdCl₂/active carbon | None | 105 | 400 | 12.9 | 17.8 | 18.6 | 17.5 | 16.1 | 14.9 |
| 10* | PdCl₂—CuCl₂/titanium oxide | 300 | 125 | 870 | 13.6 | 12.2 | 10.1 | 9.4 | — | — |
| 11* | PdCl₂—CuCl₂/magnesia | 300 | 125 | 380 | 0.6 | 0.9 | 0.4 | 0.4 | — | — |

*Comparative Example

EXAMPLE 2

To 200 ml of water were added 1.60 g of palladium chloride dihydrate and 12.8 g of cupric chloride dihydrate; the mixture was heated at 60° C. to prepare a solution. 40 g of alumina (manufactured by Sumitomo Kagaku K.K., Trade Mark: KHA 24) was added to the resultant solution; the mixture was stirred for 2 hours, dried under reduced pressure and calcined at various temperatures in air to prepare the catalysts. The content of palladium in the catalyst was 2.0% by weight based on the carrier of alumina and the Cu/Pd atomic ratio was 10.

The oxidation of 1-butene was continuously carried out at 125° C. and various space velocities with 20 g of the so prepared catalyst and the same apparatus and mixed gas as those of Example 1, whereby the results shown in Table II were obtained. The composition of the reaction product after a running time of 4 hours in Run No. 15, for example, is shown below and scarcely any changes are found therein with the running time.

Conversion ratio of butene: 53.2%

Selectivities to reaction products:

MEK 89.3%, n-butyl aldehyde 2.4%, propionaldehyde 0.8%, acetaldehyde 0.5%, acetic acid 1.1%, carbon dioxide 1.5%

No chlorobutanone and chlorinated products of butene were found.

For comparison, 1-butene was oxidized by the same method and procedure as mentioned above except that a catalyst was used prepared similarly but not calcined (Run No. 19), but the deterioration of this catalyst after being used for a long time was greater as compared with the calcined catalyst as shown in Table II.

The oxidation reaction was carried out with 20 g of the so prepared catalyst and the same apparatus as used in Example 1, at a reaction temperature of 125° C. by feeding a mixed gas of 1-butene, air and steam in a proportion by volume of 1 : 5 : 10 at a space velocity of 600 1/1-catalyst-hr. The results are shown in Table III.

TABLE III

| Reaction time(hr.) | 2 | 4 | 6 | 8 | 24 |
|---|---|---|---|---|---|
| MEK Yield (%) | 54.0 | 50.3 | 48.2 | 42.7 | 33.0 |

EXAMPLE 4

A catalyst of palladium chloride-copper chloride/silica was prepared by forming pellets having a Cu/Pd ratio of 12.0 in a manner similar to that of Example 1 but with the use of cuprous chloride in place of cupric chloride. The pellets were then calcined at 300° C. in air for 6 hours. The oxidation reaction of a gas mixture of 1-butene, air and steam in a proportion by volume of 1 : 5 : 10 was carried out with 20 g. of this catalyst at a reaction temperature of 125° C. and a space velocity of

TABLE II

| Run No. | Catalyst | Calcining temp. (° C) | Reaction temp. (° C) | Space velocity (hr$^{-1}$) | Yield of MEK (%) Running time (hrs.) | | | | | |
|---|---|---|---|---|---|---|---|---|---|---|
| | | | | | 2 | 4 | 6 | 8 | 24 | 48 |
| 12 | PdCl$_2$—CuCl$_2$/alumina | 300 | 125 | 400 | 70.0 | 68.1 | 66.4 | 64.0 | 60.8 | 58.8 |
| 13* | " | 120 | " | 720 | 42.7 | 37.8 | 32.8 | 26.6 | 21.6 | 18.8 |
| 14 | " | 200 | " | " | 44.0 | 42.7 | 42.0 | 38.1 | 34.1 | 32.5 |
| 15 | " | 300 | " | " | 46.2 | 47.5 | 43.1 | 39.0 | 35.0 | 32.9 |
| 16 | " | 400 | " | " | 42.4 | 41.9 | 39.7 | 33.3 | 31.2 | 30.7 |
| 17* | " | 450 | " | " | 19.3 | 20.1 | 20.7 | 19.1 | 17.7 | 17.0 |
| 18 | " | 300 | " | 1100 | 40.1 | 36.2 | 32.5 | 29.8 | 28.0 | 26.3 |
| 19* | " | None | " | 720 | 41.9 | 40.0 | 38.6 | 37.0 | 24.9 | 14.7 |

*Comparative Example

EXAMPLE 3

1.6 g o. palladium chloride dihydrate was dissolved in 100 ml of 0.1 N hydrochloric acid, mixed with 35 ml of an aqueous solution of hydrazine and sodium bicarbonate (hydrazine 3% by weight + sodium bicarbonate 4% by weight) to reduce palladium chloride and the resultant black precipitate was separated by filtration followed by washing with water until no chloride ion was found. The reduced palladium was added to a solution containing 6.4 g of cupric chloride dihydrate and 133 g of an aqueous colloidal silica, stirred adequately at 60° C. for 2 hours, dried at 80° C. under reduced pressure, formed into pellets of 3 mm diameter and calcined at 300° C. in air for 6 hours to prepare the catalyst. The content of palladium (metal weight %) in this catalyst was 2.0% based on the carrier of silica and the Cu/Pd atomic ratio was 5.0.

640 1/1-catalyst-hr., whereby the results shown in Table IV were obtained.

TABLE IV

| Reaction time(hr.) | 2 | 4 | 8 | 24 |
|---|---|---|---|---|
| MEK Yield (%) | 48.8 | 46.7 | 47.3 | 42.6 |

EXAMPLE 5

In the step of preparing the catalyst in accordance with Example 1, ammonium metavanadate (NH$_4$VO$_3$), vanadyl (IV) chloride (VOCl$_2$), vanadium (III) chloride (VCl$_3$), silver chloride (AgCl) or cerium (III) chloride was added as a third component and the resulting mixture was formed into pellets and then calcined at 300° C. in air for 6 hours to prepare the catalyst. The oxidation of 1-butene was carried out with 20 g. of the so-obtained catalyst in a manner similar to that of Example 1. The results are shown in Table V.

TABLE V

| Third Component | Catalyst (Atomic Ratio) | Reaction Temp. (° C.) | Space Velocity (hr$^{-1}$) | MEK Yield (%) Reaction Time (hr.) | | | |
|---|---|---|---|---|---|---|---|
| | | | | 2 | 4 | 8 | 24 |
| NH$_4$VO$_3$ | Pd : Cu : V (1 : 5 : 0.5) | 125 | 640 | 49.0 | 50.2 | 48.4 | 46.0 |
| VOCl$_2$ | Pd : Cu : V (1 : 5 : 0.4) | 125 | 640 | 51.6 | 52.4 | 51.0 | 49.0 |
| VCl$_3$ | Pd : Cu : V (1 : 5 :0.7) | 125 | 640 | 52.1 | 54.2 | 47.0 | 43.6 |
| AgCl | Pd : Cu : Ag (1 : 5 : 0.7) | 125 | 640 | 60.2 | 61.2 | 59.3 | 56.0 |
| CeCl$_3$ | Pd : Cu : Ce | 125 | 640 | 59.0 | 59.5 | 56.7 | 52.3 |

TABLE V-continued

| Third Component | Catalyst (Atomic Ratio) | Reaction Temp. (° C.) | Space Velocity (hr⁻¹) | MEK Yield (%) Reaction Time (hr.) | | | |
|---|---|---|---|---|---|---|---|
| | | | | 2 | 4 | 8 | 24 |
| | (1 : 5 : 0.2) | | | | | | |

EXAMPLE 6

The oxidation of cis-2-butene was carried out with 20 g. of the catalyst used in Run No. 4 of Example 1, and in a manner similar to that of Example 1. After a running time of 4 hours, MEK was obtained with a yield of 19.5%, butene conversion ratio of 20.7% and MEK selectivity of 94.2%. Simultaneously by-products were formed with selectivities of n-butyl aldehyde 0.4%, acetaldehyde 0.6%, acetic acid 1.0% and carbon dioxide 1.5%.

EXAMPLE 7

The oxidation of a spent $C_4$-fraction comprising 53.4% by volume of 1-butene, 15.8% by volume of trans-2-butene, 10.8% by volume of cis-2-butene, 16.3% by volume of n-butane and 2.7% by volume of isobutane was carried out with 20 g. of the catalyst used in Run No. 4 of Example 1 and in a manner similar to that of Example 1. The spent $C_4$-Fraction was obtained by extracting and removing butadiene and isobutene from a $C_4$ fraction from a naphtha steam-cracking plant.

After a running time of 4 hours, MEK was produced with a yield of 29.6%, butene conversion ratio of 33.4% and MEK selectivity of 88.6%.

What we claim is:

1. A process for the preparation of a catalyst composition useful for the production of carbonyl compounds by reacting olefins with oxygen in the presence of steam, which process consists essentially of calcining at a temperature of 200° to 400° C. a catalyst composition comprising palladium and/or palladium compounds, copper chloride and a carrier selected from the group consisting of silica, alumina and silica-alumina and, without a hydrogenation step, recovering an oxidation catalyst product.

2. The process of claim 1 wherein said catalyst composition is prepared by providing on said carrier palladium and/or palladium compounds and copper chloride.

3. The process of claim 1 wherein said catalyst composition is prepared by mixing palladium and/or palladium compounds and copper chloride with said carrier and forming the resulting mixture.

4. A process for the preparation of a catalyst composition useful for the production of carbonyl compounds by reacting olefins with oxygen in the presence of steam which process consists essentially of calcining at a temperature of 200° to 400° C. a catalyst composition comprising palladium and/or palladium compounds, copper chloride, one or more compounds selected from the group consisting of silver, cerium and vanadium compounds and a carrier selected from the group consisting of silica, alumina and silica-alumina and, without a hydrogenation step, recovering an oxidation catalyst product.

5. The process of claim 4 wherein said catalyst composition is prepared by providing on said carrier palladium and/or palladium compounds, copper chloride and one or more compounds selected from the group consisting of silver, cerium and vanadium compounds.

6. The process of claim 4 wherein said catalyst composition is prepared by mixing palladium and/or palladium compounds, copper chloride and one or more compounds selected from the group consisting of silver, cerium and vanadium compounds with said carrier and forming the resulting mixture.

7. The catalyst whenever made by the process of claim 1.

* * * * *